United States Patent [19]
Kawabe et al.

[11] Patent Number: 5,318,875
[45] Date of Patent: Jun. 7, 1994

[54] POSITIVE QUINONEDIAZIDE PHOTORESIST COMPOSITION CONTAINING SELECT HYDROXYPHENOL ADDITIVE

[75] Inventors: Yasumasa Kawabe; Toshiaki Aoai; Tadayoshi Kokubo; Shiro Tan, all of Shizuoka, Japan

[73] Assignee: Fuji Photo Film Co., Ltd., Kanagawa, Japan

[21] Appl. No.: 15,921

[22] Filed: Feb. 10, 1993

[30] Foreign Application Priority Data

Feb. 12, 1992 [JP] Japan .................................. 4-25157
Apr. 23, 1992 [JP] Japan ................................. 4-104542
Apr. 27, 1992 [JP] Japan ................................. 4-107888

[51] Int. Cl.$^5$ .......................... G03F 7/023; G03C 1/61
[52] U.S. Cl. .................................... 430/191; 430/165; 430/192
[58] Field of Search ............... 430/191, 190, 192, 193, 430/165

[56] References Cited

U.S. PATENT DOCUMENTS 4,514,334  4/1985  Mark ...................... 552/108
5,112,719  5/1992  Yamada et al. ............ 430/191
5,188,920  2/1993  Moriuma et al. .......... 430/191

FOREIGN PATENT DOCUMENTS 0416544  3/1991  European Pat. Off. .
0477691  4/1992  European Pat. Off. .

Primary Examiner—Charles L. Bowers, Jr.
Assistant Examiner—Christopher G. Young
Attorney, Agent, or Firm—Sughrue, Mion, Zinn, Macpeak & Seas

[57] ABSTRACT

A positive photoresist composition includes an alkali-soluble resin, a quinonediazide compound and a compound selected from the group consisting of compounds represented by formulae (I), (II) and (III):

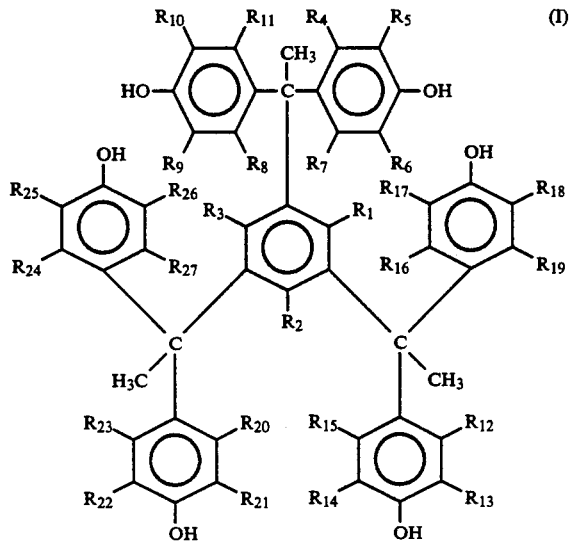

wherein $R_1$ to $R_{27}$, which may be the same or different, each represents a hydrogen atom, hydroxyl group, halogen atom, alkyl group, alkoxy group, nitro group, alkenyl group, aryl group, aralkyl group, alkoxycarbonyl group, arylcarbonyl group, acyloxy group, acyl group, aryloxy group or aralkoxy group;

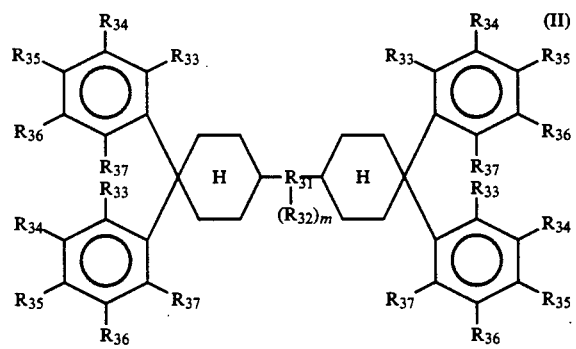

wherein $R_{31}$ represents an organic group, single bond, (Abstract continued on next page.)

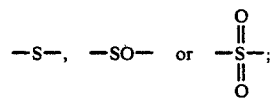

$R_{32}$ represents a hydrogen atom, monovalent organic group or

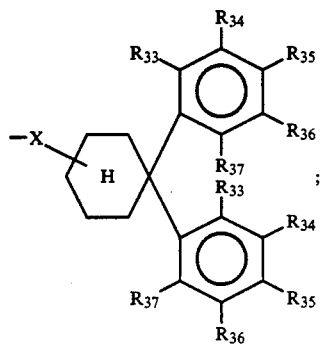

$R_{33}$ to $R_{37}$, which may be the same or different, and in which not all four groups for each of $R_{33}$ to $R_{37}$ may be the same at the same time, each represents a hydrogen atom, hydroxyl group, halogen atom, alkyl group, alkoxy group or alkenyl group, with the proviso that at least one of $R_{33}$ to $R_{35}$ is a hydroxyl group; X represents a divalent organic group; and m represents an integer 0 or 1;

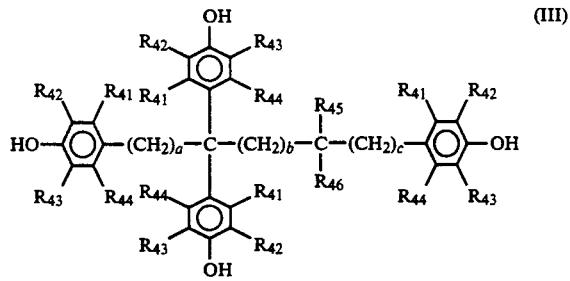

wherein $R_{41}$ to $R_{44}$, which may be the same or different and in which not all four groups for each of $R_{41}$ to $R_{44}$ may be the same at the same time, each represents a hydrogen atom, hydroxyl group, halogen atom, alkyl group, alkoxy group or alkenyl group; $R_{45}$ and $R_{46}$ each represents a hydrogen atom, alkyl group or

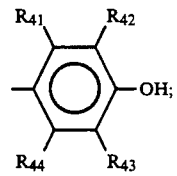

a and c each represents an integer 0 or 1; and b represents an integer from 1 to 4.

5 Claims, No Drawings

POSITIVE QUINONEDIAZIDE PHOTORESIST COMPOSITION CONTAINING SELECT HYDROXYPHENOL ADDITIVE

FIELD OF THE INVENTION

The present invention relates to a positive-type photoresist composition sensitive to radiation. More particularly, the present invention relates to a photoresist composition for fine work which provides high resolution and sensitivity and an excellent pattern sectional shape.

The positive-type photoresist of the present invention is coated on a substrate such as semiconductor wafer, glass, ceramic or metal by a spin coating method or a roller coating method to a thickness of about 0.5 to 3 μm. The coated material is then heated and dried. A circuit pattern or the like is imagewise formed in the material through an exposure mask by irradiation with ultraviolet rays. The material is then subjected to development to obtain a positive image. Subsequently, the positive image is used as a mask to effect patterned etching on a substrate. Typical applications of positive-type photoresist are the production of semiconductors such as integrated circuits (IC), the production of circuit boards such as liquid crystals and thermal heads, and photofabrication.

BACKGROUND OF THE INVENTION

Compositions comprising an alkali-soluble resin and a naphthoquinonediazido compound as a light-sensitive material are normally used as positive-type photoresist compositions. Examples of such compositions include novolak-type phenol resin/naphthoquinonediazido-substituted compounds as disclosed in U.S. Pat. Nos. 3,666,473, 4,115,128 and 4,173,470. Most typical examples of such compositions include novolak resins made of cresol-formaldehyde/trihydroxybenzophenone-1,2-naphthoquinonediazidosulfonic ester as disclosed in L. F. Thompson, *Introduction to Microlithography*, No. 219, pages 112 to 121, published by ACS.

As a binder, novolak resins can be dissolved in alkaline aqueous solutions without swelling. The novolak resin can also exhibit a high resistance, particularly to plasma etching, when an image thus produced is used as a mask for etching. Thus, novolak resins are particularly useful in this application. As a light-sensitive material, a naphthoquinonediazido compound itself serves as a dissolution inhibitor for reducing the alkali solubility of novolak resins but is peculiar in that it undergoes decomposition upon irradiation with light to produce an alkali-soluble substance which rather enhances the alkali solubility of novolak resin. Because of the great change in properties by the irradiation with light, the naphthoquinonediazido compound is particularly useful as the light-sensitive material for a positive-type photoresist.

From such a perspective, many positive-type photoresists comprising novolak resin and naphthoquinonediazido light-sensitive material have heretofore been developed and put to practical use. These positive-type photoresists have attained sufficient results in forming lines having a width as small as 1.5 to 2 μm.

However, integrated circuits have further increased in degree of integration. In the production of semiconductor boards for applications such as SLSI, it has been required to form very fine patterns having a line width of 1 μm or less. In such applications, a high sensitivity photoresists are desired from the viewpoints of particularly high resolution, high precision in producing patterns for exactly copying the shape of the exposure mask, and high productivity.

It is a recent tendency that the etching process is switched from a wet etching process to a dry etching process to improve resolution and enhance the degree of integration in integrated circuits. However, since the dry etching process is subjected to an increase in the temperature of the resist, the resist to be used in this process is required to exhibit a high heat-resistance to avoid heat deforamtion.

Examples of approaches for improving the heat resistance of the resist include the use of a resin free of components with a weight-average molecular weight of 2,000 or less as disclosed in JP-A-60-97347 (the term "JP-A" as used herein means an "unexamined published Japanese patent application") and the use of resin wherein the total content of monomers, dimers and trimers is 10% by weight or less as disclosed in JP-A-60-189739.

However, the use of the above-mentioned resin free of or having a reduced amount of low molecular weight components is disadvantageous in that it normally causes a reduction in sensitivity, lowering the throughput in the production of devices.

It has been attempted to improve the sensitivity or developability of a resist composition by incorporating specified compounds into the resist composition. For example, U.S. Pat. Nos. 4,738,915, 4,626,492 and 4,424,270 disclose a positive-type photoresist composition containing trihydroxybenzophenone. The use of such a positive-type photoresist composition containing trihydroxybenzophenone enables improvements in sensitivity and developability but is disadvantageous in that the incorporation of trihydroxybenzophenone causes deterioration in the heat resistance of the composition.

In approaches as disclose in European Patent 301332, JP-A-1-177032, JP-A-1-280748, and U.S. Pat. No. 5,077,173, an aromatic polyhydroxy compound other than trihydroxybenzophenone is used to provide a higher sensitivity without causing any deterioration in the heat resistance. However, these approaches do not result in any improvement in developability.

SUMMARY OF THE INVENTION

It is therefore an object of the present invention to provide a positive-type, photoresist composition which can provide a resist pattern having high resolution and developability and an excellent heat resistance in the production of semiconductor devices.

Taking these requirements into account, the inventors made extensive studies. As a result, it was found that the above mentioned object of the present invention can be accomplished by the use of an alkali-soluble resin, a quinone diazide compound and a compound having a specific structural formula. Thus, the present invention was worked out on the basis of this knowledge.

More specifically, the object of the present invention is accomplished with a positive photoresist composition, which comprises an alkali-soluble resin, a quinonediazide compound and a compound selected from the group consisting of compounds represented by formulae (I), (II) and (III):

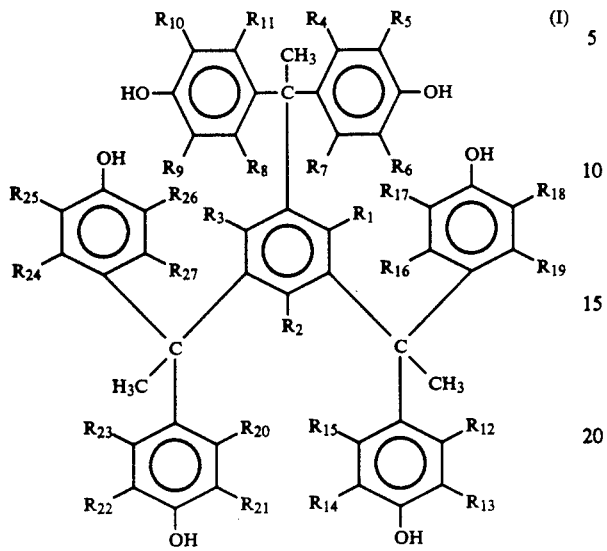
(I)

wherein $R_1$ to $R_{27}$, which may be the same or different, each represents a hydrogen atom, hydroxyl group, halogen atom, alkyl group, alkoxy group, nitro group, alkenyl group, aryl group, aralkyl group, alkoxycarbonyl group, arylcarbonyl group, acyloxy group, acyl group, aryloxy group or aralkoxy group;

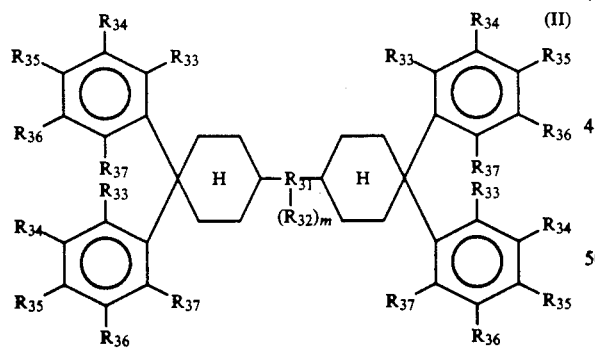
(II)

wherein $R_{31}$ represents an organic group, single bond,

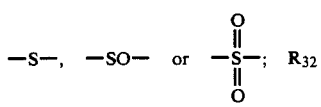
; $R_{32}$ represents a hydrogen atom, monovalent organic group or

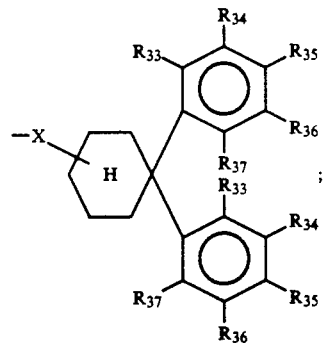
;

$R_{33}$ to $R_{37}$ which may be the same or different and in which not all four groups for each of $R_{33}$ to $R_{37}$ may be the same at the same time, each represents a hydrogen atom, hydroxyl group, halogen atom, alkyl group, alkoxy group or alkenyl group, with the proviso that at least one of $R_{33}$ to $R_{35}$ is a hydroxyl group; X represents a divalent organic group; and m represents an integer 0 or 1;

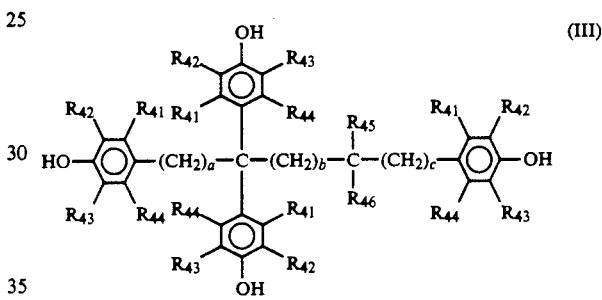
(III)

wherein $R_{41}$ to $R_{44}$, which may be the same or different and in which not all four groups for each of $R_{41}$ to $R_{44}$ may be the same at the same time, each represents a hydrogen atom, hydroxyl group, halogen atom, alkyl group, alkoxy group or alkenyl group; $R_{45}$ and $R_{46}$ each represents a hydrogen atom, alkyl group or

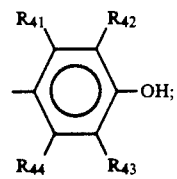
;

a and c each represents an integer 0 or 1; and b represents an integer from 1 to 4.

DETAILED DESCRIPTION OF THE INVENTION

The present invention will be further described hereinafter.

In formula (I), the halogen atom represented by any of $R_1$ to $R_{27}$ is preferably a chlorine atom, bromine atom or iodine atom. The alkyl group represented by any of $R_1$ to $R_{27}$ is preferably a $C_{1-4}$ alkyl group such as a methyl group, ethyl group, propyl group, n-butyl group, isobutyl group, sec-butyl group or t-butyl group. The alkoxy group represented by any of $R_1$ to $R_{27}$ is preferably a $C_{1-4}$ alkoxy group such as a methoxy group, ethoxy group, hydroxyethoxy group, propoxy group, hydroxypropoxy group, isopropoxy group, n-butoxy group, isobutoxy group, sec-butoxy group or t-butoxy group. The alkenyl group represented by any of $R_1$ to $R_{27}$ is preferably a $C_{2-4}$ alkenyl group such as a vinyl group, propenyl group, allyl group or butenyl group.

The aryl group represented by any of $R_1$ to $R_{27}$ is preferably a phenyl group, xylyl group, toluyl group or cumenyl group. The aralkyl group represented by any of $R_1$ to $R_{27}$ is preferably a benzyl group, phenethyl group or cumyl group. The alkoxycarbonyl group represented by any of $R_1$ to $R_{27}$ is preferably a methoxycarbonyl group or ethoxycarbonyl group. The arylcarbonyl group represented by any of $R_1$ to $R_{27}$ is preferably a benzoyloxy group. The acyloxy group represented by any of $R_1$ to $R_{27}$ is preferably a butyryloxy group or acetoxy group. The acyl group represented by any of $R_1$ to $R_{27}$ is preferably a formyl group, acetyl group, butyryl group, benzoyl group, cyanamoyl group or valeryl group. The aryloxy group represented by any of $R_1$ to $R_{27}$ is preferably a benzyloxy group. The aralkoxy group represented by any of $R_1$ to $R_{27}$ is preferably a phenoxy group.

In formula (II), the halogen atom represented by any of $R_{33}$ to $R_{37}$ is preferably a chlorine atom, bromine atom or iodine atom. The alkyl group represented by any of $R_{33}$ to $R_{37}$ is preferably a $C_{1-4}$ alkyl group such as a methyl group, ethyl group, propyl group, n-butyl group, isobutyl group, sec-butyl group or t-butyl group. The alkoxy group represented by any of $R_{33}$ to $R_{37}$ is preferably a $C_{1-4}$ alkoxy group such as a methoxy group, ethoxy group, hydroxyethoxy group, propoxy group, hydroxypropoxy group, isopropoxy group, n-butoxy group, isobutoxy group, sec-butoxy group or t-butoxy group. The alkenyl group represented by any of $R_{33}$ to $R_{37}$ is preferably a $C_{2-4}$ alkenyl group such as a vinyl group, propenyl group, allyl group or butenyl group.

The organic group represented by $R_{31}$ is preferably a lower alkylene group, the monovalent organic group represented by $R_{32}$ is preferably a lower alkyl group, and the divalent organic group represented by X is preferably a lower alkylene group.

In formula (III), the halogen atom represented by any of $R_{41}$ to $R_{44}$ is preferably a chlorine atom, bromine atom or iodine atom. The alkyl group represented by any of $R_{41}$ to $R_{44}$ is preferably a $C_{1-4}$ alkyl group such as a methyl group, ethyl group, propyl group, n-butyl group, isobutyl group, sec-butyl group or t-butyl group. The alkoxy group represented by any of $R_{41}$ to $R_{44}$ is preferably a $C_{1-4}$ alkoxy group such as a methoxy group, ethoxy group, hydroxyethoxy group, propoxy group, hydroxypropoxy group, isopropoxy group, n-butoxy group, isobutoxy group, sec-butoxy group or t-butoxy group. The alkenyl group represented by any of $R_{41}$ to $R_{44}$ is preferably a $C_{2-4}$ alkenyl group such as a vinyl group, propenyl group, allyl group or butenyl group.

The compounds represented by formula (I) can be obtained by, e.g., the method described in U.S. Pat. Nos. 4,426,513 and 4,514,334, that is, by allowing a carbonyl precursor and a phenol derivative to undergo reaction under acidic or alkaline conditions.

If the above reaction is effected under acidic conditions, a catalyst containing a mercapto group is preferably used. Examples of such a catalyst include ethanethiol, 1-butanethiol, thiophenol, and mercaptoacetic acid. In the above condensation reaction, the phenol reactive component is preferably used in an amount exceeding the stoichiometrical value. The reaction temperature is preferably in the range of room temperature or higher, more preferably about 100° C. or higher.

The progress of the condensation reaction can be monitored by chromatography or spectroscopy. For example, infrared spectroscopy can be employed to trace the progress of the condensation reaction easily by the reduction of the carbonyl absorption band.

The purification o these compounds can be carried out by recrystallization, elution chromatography or the like.

Examples of solvents suitable for recrystallization include methylene chloride, benzene, cyclohexane, methanol, ethanol, and mixtures of alcohol and water.

The elution chromatography is preferably effected through alumina or silica with various solvents as eluents.

Specific examples of the compounds represented by formula (I) include $\alpha,\alpha,\alpha',\alpha',\alpha'',\alpha''$-hexakis-(4-hydroxyphenyl)-1,3,5-triethylbenzene, $\alpha,\alpha,\alpha',\alpha',\alpha'',\alpha''$-hexakis-(4-hydroxy-2,6-dimethylphenyl)-1,3,5-triethylbenzene, $\alpha,\alpha,\alpha',\alpha',\alpha'',\alpha''$-hexakis-(4-hydroxy-3,5-dimethylphenyl)-1,3,5-triethylbenzene, and $\alpha,\alpha,\alpha',\alpha',\alpha'',\alpha''$-hexakis-(4-hydroxy-3-methylphenyl)-1,3,5-triethylbenzene. However, the present invention should not be construed as being limited thereto.

These compounds may be used singly or in combination.

The compounds represented by formula (II) can be synthesized in accordance with, e.g., the method disclosed in JP-A-49-250. More particularly, the compound represented by formula (II) can be obtained by allowing a biscyclohexanone or triscyclohexanone compound represented by formula (IV) and a phenol compound represented by formula (V) to undergo reaction:

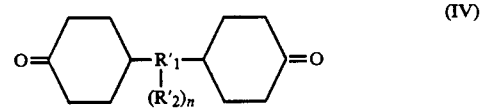

(IV)

wherein $R'_1$ represents an organic group, single bond,

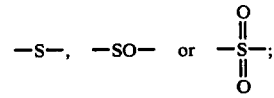

$R'_2$ represents a hydrogen atom, monovalent organic group or

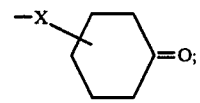

X represents a divalent organic group; and n represents an integer 0 or 1.

The organic group represented by $R'_1$ is preferably a lower alkylene group, the monovalent organic group represented by $R'_2$ is preferably a lower alkyl group, and the divalent organic group represented by X is preferably a lower alkylene group.

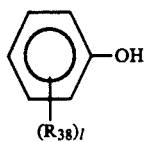

(V)

wherein $R_{38}$ represents a hydrogen atom, hydroxyl group, halogen atom, alkyl group, alkoxy group or alkenyl group; and l represents an integer from 1 to 4.

The biscyclohexanone or triscyclohexanone compound to be used in the above mentioned synthesis can be easily synthesized by, e.g., oxidizing hydrogenated bisphenol or hydrogenated trisphenol with a bichromate or the like.

In A. Terada, *Bulletin of the Chemical Society of Japan*, Vol. 39, No. 10, p. 2,195 (1966), hydrogenated bisphenol is oxidized with chromic anhydride to synthesize biscyclohexanone. The phenol compound used as the other starting material is on the market as an industrial material today and is thus easily available.

Examples of catalysts to be used in the reaction of the phenol compound with the biscyclohexanone or triscyclohexanone compound in the present invention include inorganic acids such as phosphoric acid, sulfuric acid and hydrochloric acid, protonic acids such as benzenesulfonic acid and paratoluenesulfonic acid, and halides of certain kind of metallic ions such as zinc, iron, copper, cobalt and manganese ions. Further, hydroxides or phenolic salts of alkaline metals can be used.

Alternatively, a co-catalyst containing a mercapto group such as ethanethiol, 1-butanethiol, thiophenol or mercaptoacetic acid may be used.

In the above reaction of the biscyclohexanone or triscyclohexanone compound with the phenol compound, the phenol reactive component is preferably used in an amount exceeding the stoichiometrical value. In this reaction, the molar ratio of the biscyclohexanone starting material to the phenol compound is preferably in the range of about 1:4 to about 1:30, and the molar ratio of the triscyclohexanone starting material to the phenol compound is preferably in the range of about 1:6 to about 1:40.

The reaction temperature is preferably in the range of about 0° C. to about 150° C. The progress of the reaction can be monitored by chromatography or spectroscopy.

Specific examples of the compounds represented by formula (II) include those represented by formulae [II-a] to [II-k], but the present invention should not be construed as being limited thereto.

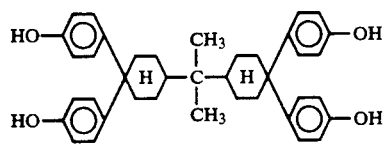
[II-a]

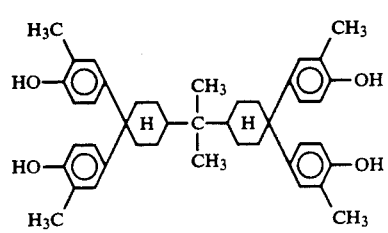
[II-b]

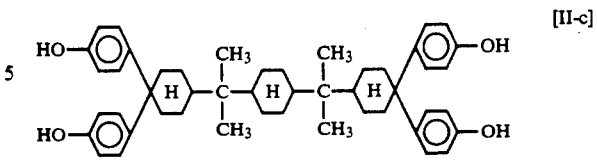
[II-c]

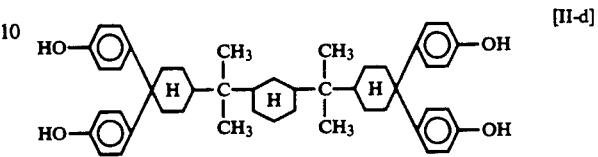
[II-d]

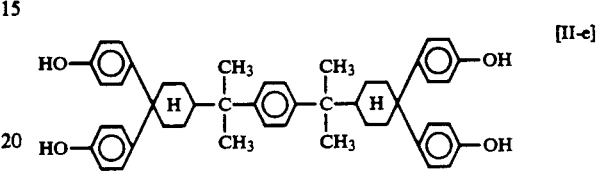
[II-e]

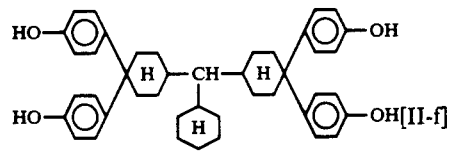
[II-f]

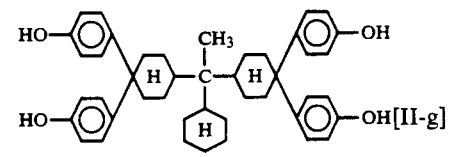
[II-g]

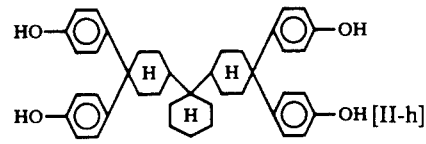
[II-h]

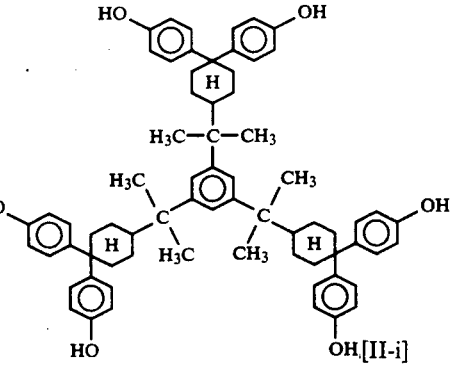
[II-i]

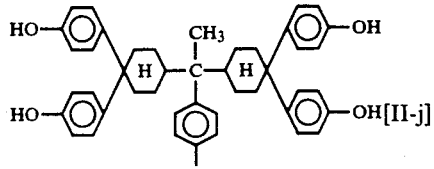
[II-j]

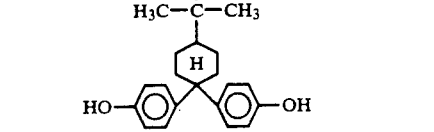

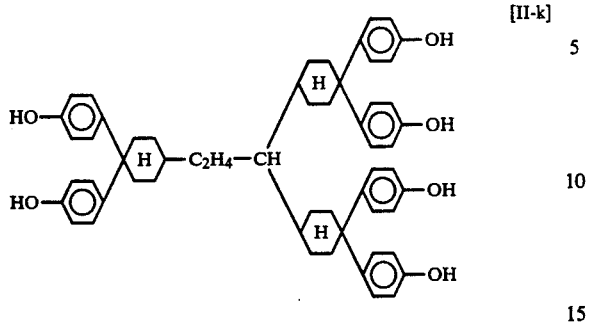
[II-k]

The compounds represented by formula (III) can be obtained by, e.g., the method described in U.S. Pat. Nos. 4,426,513 and 4,514,334, that is, by allowing a carbonyl precursor and a phenol derivative to undergo reaction under acidic or alkaline conditions, using a p-hydroxyphenylketone compound obtained by, e.g., the method described in *Chemishe Berichte*, Vol. 74, p. 1,772 (1941).

Alternatively, the compounds represented by formula (III) can be obtained by, e.g., the method described in U.S. Pat. No. 2,965,611, that is, by allowing a haloketone compound and a phenol derivative to undergo reaction under acidic conditions.

If the above reaction is effected under acidic conditions, a catalyst containing a mercapto group is preferably used. Examples of such a catalyst include ethanethiol, 1-butanethiol, thiophenol, and mercaptoacetic acid, but the present invention should not be construed as being limited thereto. In the above condensation reaction, the phenol reactive component is preferably used in an amount exceeding the stoichiometrical value. The reaction temperature is preferably in the range of room temperature or higher, more preferably about 100° C. or higher.

The progress of the condensation reaction can be monitored by chromatography or spectroscopy. For example, infrared spectroscopy can be employed to trace the progress of the condensation reaction easily by the reduction of the carbonyl absorption band.

The purification of these compounds can be carried out by recrystallization, elution chromatography or the like.

Examples of solvents suitable for recrystallization include methylene chloride, benzene, cyclohexane, methanol, ethanol, and mixtures of alcohol and water.

The elution chromatography is preferably effected through alumina or silica with various solvents as eluents.

Specific examples of the compounds represented by formula (III) include those represented by formulae [III-a] to [III-p], but the present invention should not be construed as being limited thereto.

These polyhydroxy compounds can be used singly or in combination.

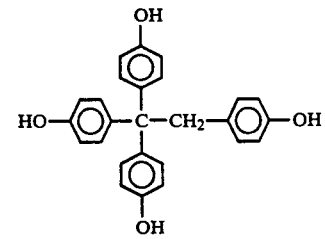
[III-a]

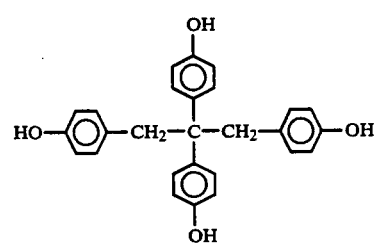
[III-b]

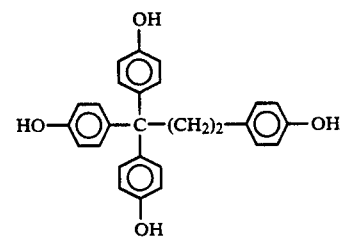
[III-c]

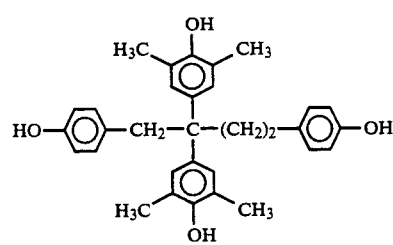
[III-d]

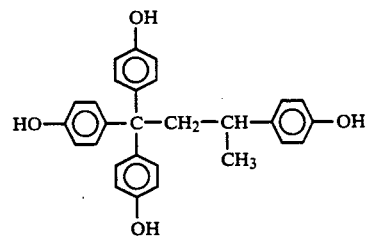
[III-e]

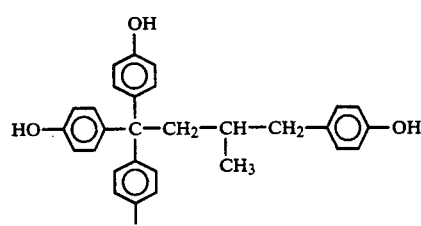
[III-f]

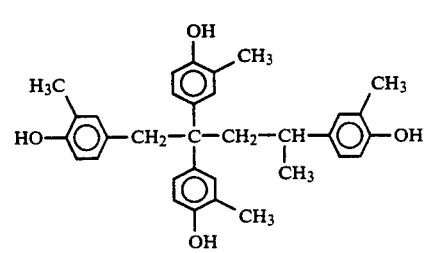
[III-g]

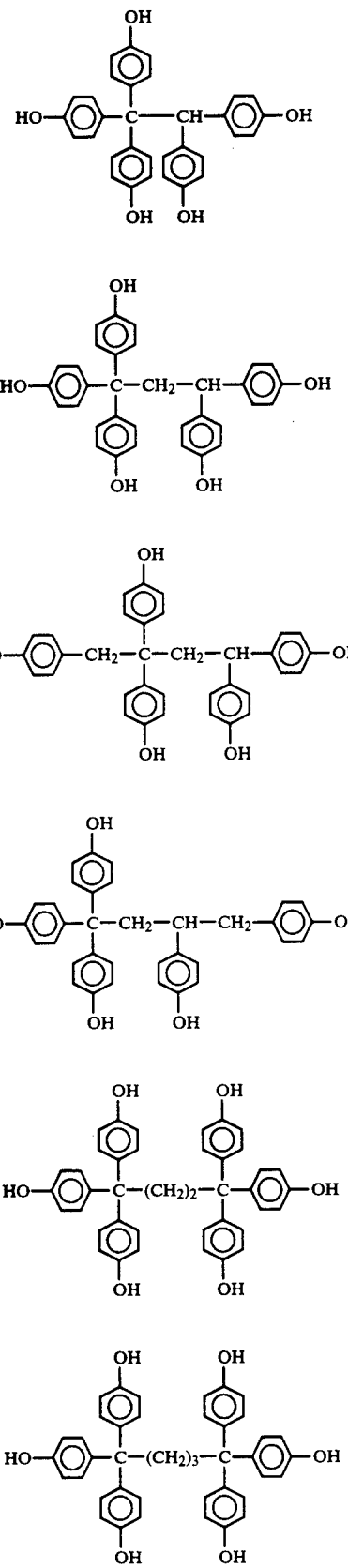

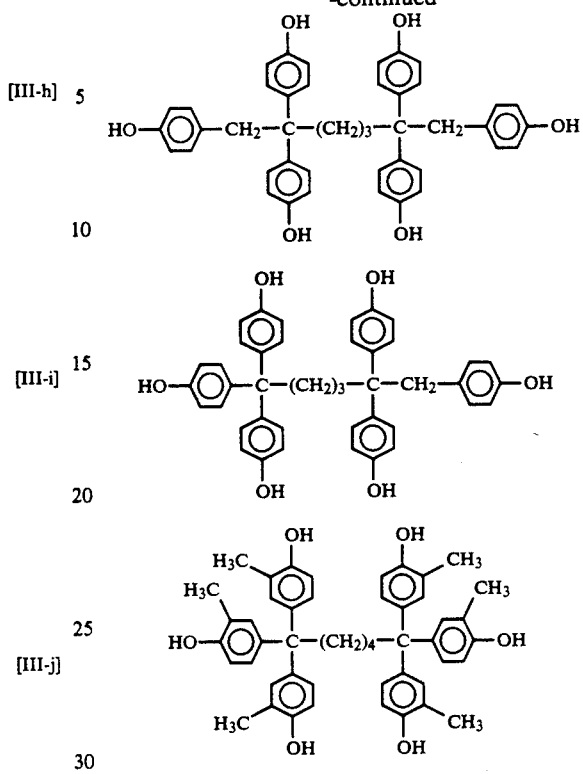

The amount of the compound selected from the group consisting of compounds represented by formula (I), (II) and (III) is normally in the range of about 150 parts by weight or less, preferably about 5 to about 100 parts by weight based on 100 parts by weight of quinonediazide compound. If this proportion falls below about 5 parts by weight, the sensitivity increase cannot be substantially obtained. In contrast, if this proportion exceeds 150 parts by weight, the percent film remaining is remarkably reduced.

Examples of the alkali-soluble resins to be used in the present invention include novolak resins, acetone-pyrogallol resins, polyhydroxystyrene, and derivatives thereof.

Particularly preferred among these compounds are novolak resins. Such novolak resins can be obtained by addition condensation of predetermined monomers as main components with aldehydes in the presence of an acidic catalyst.

As such predetermined monomers there can be used, singly, or in admixture, phenol; cresols such as m-cresol, p-cresol and o-cresol; xylenols such as 2,5-xylenol, 3,5-xylenol, 3,4-xylenol and 2,3-xylenol; alkylphenols such as m-ethylphenol, p-ethylphenol, o-ethylphenol and p-t-butylphenol; alkoxyphenols such as p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol and p-butoxyphenol; bisalkylphenols such as 2-methyl-4-isopropylphenol; and hydroxyaromatic compounds such as m-chlorophenol, p-chlorophenol, o-chlorophenol, dihydroxybiphenyl, bisphenol A, phenylphenol, resorcinol and naphthol. However, the present invention should not be construed as being limited thereto.

Examples of aldehydes to be used in addition condensation include formaldehyde, paraformaldehyde, acetaldehyde, propylaldehyde, benzaldehyde, phenylacetaldehyde, α-phenylpropylaldehyde, β-phenylpropylaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, p-nitrobenzaldehyde, o-methylbenzaldehyde, m-methylbenzaldehyde, p-methylbenzaldehyde, p-ethylbenzaldehyde, p-n-butylbenzaldehyde, furfural, chloroacetaldehyde and acetal compounds thereof such as chloroacetaldehydediethylacetal. Among these compounds, formaldehyde can be preferably used.

These aldehydes are used singly or in combination.

Examples of acidic catalysts to be used in the addition condensation include hydrochloric acid, sulfuric acid, formic acid, acetic acid, and oxalic acid.

The weight average molecular weight of the novolak resin thus obtained is preferably in the range of about 2,000 to about 30,000, particularly about 6,000 to about 20,000. If this value falls below about 2,000, the loss of film on unexposed portions after development becomes too great. If this value exceeds about 30,000, the development speed is too low. The particularly preferred molecular weight range is from about 6,000 to about 20,000.

The weight average molecular weight as specified herein is represented as calculated in terms of polystyrene determined by gel permeation chromatography.

The light-sensitive material to be used in the present invention can comprise a compound obtained by esterification of a polyhydroxy compound set forth below with 1,2-naphthoquinonediazido-5-(and/or -4-)sulfonyl chloride.

Examples of such a polyhydroxy compound include polyhydroxybenzophenones such as 2,3,4-trihydroxybenzophenone, 2,4,4'-trihydroxybenzophenone, 2,4,6-trihydroxybenzophenone, 2,3,4-trihydroxy-2'-methylbenzophenone, 2,3,4,4'-tetrahydroxybenzophenone, 2,2',4,4'-tetrahydroxybenzophenone, 2,4,6,3',4'-pentahydroxybenzophenone; 2,3,4,2',4'-pentahydroxybenzophenone, 2,3,4,2',5'-pentahydroxybenzophenone, 2,4,6,3',4',5'-hexahydroxybenzophenone, and 2,3,4,3',4',5'-hexahydroxybenzophenone; polyhydroxyphenylalkylketones such as 2,3,4-trihydroxyacetophenone, 2,3,4-trihydroxyphenylpentylketone and 2,3,4-trihydroxyphenylhexylketone; bis-(poly)hydroxyphenyl)alkanes such as bis(2,4-dihydroxyphenyl)methane, bis(2,3,4-trihydroxyphenyl)methane, bis-(2,4-dihydroxyphenyl)propane-1, bis(2,3,4-trihydroxyphenyl)propane-1 and nordihydroguaiaretic acid; polyhydroxybenzoic esters such as 3,4,5-trihydroxybenzoic propoyl, 2,3,4-trihydroxybenzoic phenyl and 3,4,5-trihydroxybenzoic phenyl ester; bis(polyhydroxybenzoyl)alkanes or bis(polyhydroxybenzoyl)aryls such as bis-(2,3,4-trihydroxybenzoyl)methane, bis(3-acetyl-4,5,6-trihydroxyphenyl)-methane, bis(2,3,4-trihydroxybenzoyl)benzene and bis(2,4,6-trihydroxybenzoyl)benzene; alkylene-di(polyhydroxybenzoate) such as ethylene glycol di(3,5-dihydroxybenzoate) and ethylene glycol di(3,4,5-trihydroxybenzoate); polyhydroxybiphenyls such as 2,3,4-biphenyltriol, 3,4,5-biphenyltriol, 3,5,3',5'-biphenyltetrol, 2,4,2',4'-biphenyltetrol, 2,4,6,3',5'-biphenylpentol, 2,4,6,2',4',6'-biphenylhexol, and 2,3,4,2',3',4'- biphenylhexol; bis(polyhydroxy)sulfides such as 4,4'-thiobis(1,3-dihydroxy)benzene; bis(polyhydroxyphenyl)-ethers such as 2,2',4,4'-tetrahydroxydiphenylether; bis-(polyhydroxyphenyl)sulfoxides such as 2,2',4,4'-tetrahydroxydiphenylsulfoxide; bis(polyhydroxyphenyl)sulfones such as 2,2',4,4'-tetrahydroxydiphenylsulfone; polyhydroxytriphenylmethanes such as 4,4',3",4"-tetrahydroxy-3,5,3',5'-tetramethyltriphenylmethane, 4,4',2", 3",4"-pentahydroxy-3,5,3',5'-tetramethyltriphenylmethane, 2,3,4,2',3',4'-hexahydroxy-5,5'-diacetyltriphenylmethane, 2,3,4,2',3',4',3",4"-octahydroxy-5,5'-diacetyltriphenylmethane and 2,4,6,2',4',6'-hexahydroxy-5,5'-dipropionyltriphenylmethane; polyhydroxyspirobiindanes such as 3,3,3',3'-tetramethyl-1,1'-spirobiindane-5,6,5',6'-tetrol, 3,3,3',3'-tetramethyl-1,1'-spirobiindane-5,6,7,5',6',7'-hexol, 3,3,3',3'-tetramethyl-1,1'-spirobiindane-4,5,6,4',5',6'-hexol; and 3,3,3',3'-tetramethyl-1,1'-spirobiindane-4,5,6,5',6',7'-hexol; polyhydroxyphthalides such as 3,3-bis(3,4 -dihydroxyphenyl)phthalide, 3,3-bis(2,3,4-trihydroxyphenyl)phthalide and 3',4',5',6-tetrahydroxyspiro[phthalide-3,9'-xanthene], polyhydroxybenzopyranes such as 2-(3,4-dihydroxyphenyl)-3,5,7-trihydroxybenzopyrane, 2-(3,4,5-trihydroxyphenyl)-3,5,7-trihydroxybenzopyrane, 2-(3,4-dihydroxyphenyl)-3-(3,4,5-trihydroxybenzoyloxy)-5,7-dihydroxybenzopyrane and 2-(3,4,5-trihydroxyphenyl)-3-(3,4,5-trihydroxybenzoyloxy)-5,7-dihydroxybenzopyrane; and flavono dyes such as morin, quercetin and rutin.

Alternatively, oligomers of phenol resins such as novolak resins can be used.

These light-sensitive materials obtained by esterification of a polyhydroxy compounds with naphthoquinonediazido can be used singly or in combination.

The proportion of the light-sensitive material to the alkali-soluble resin is normally in the range of about 5 to about 100 parts by weight, preferably about 10 to about 50 parts by weight per 100 parts by weight of resin. If this value falls below about 5 parts by weight, the percent film remaining is remarkably lowered. If this value exceeds about 100 parts by weight, the sensitivity and the solubility in a solvent are lowered.

The composition of the present invention can further comprise other polyhydroxy compounds to accelerate solubility in the developer. Preferred examples of such polyhydroxy compounds include phenols, resorcin, phloroglucin, 2,3,4-trihydroxybenzophenone, 2,3,4,4'-tetrahydroxybenzophenone, 2,3,4,3',4',5'-hexahydroxybenzophenone, acetone-pyrogallol condensation resins, phloroglucide, 2,4,2',4'-biphenyltetrol, 4,4'-thiobis-(1,3-dihydroxy)benzene, 2,2',4,4'-tetrahydroxydiphenylether, 2,2',4,4'-tetrahydroxydiphenyl sulfoxide, 2,2',4,4'-tetrahydroxydiphenylsulfone, bis(2,4-dihydroxyphenyl)methane, bis(2,3,4-trihydroxyphenyl)methane, bisphenol A, bisphenol AF, bisphenol S and bisphenol F.

Such a polyhydroxy compounds can be used in an amount of about 50 parts by weight or less, preferably about 30 parts by weight or less per 100 parts by weight of polyhydroxy compound of the present invention.

Examples of solvents in which the light-sensitive material and the alkali-soluble novolak resin can be dissolved include ketones such as methyl ethyl ketone and cyclohexanone; ketoethers such as 4-ethoxy-2-butanone and 4-methoxy-4-methyl-2-pentanone; alcohol ethers such as ethylene glycol monomethyl ether and ethylene glycol monoethyl ether; ethers such as dioxane and ethylene glycol dimethyl ether; cellosolve esters such as methyl cellosolve acetate and ethyl cellosolve acetate; aliphatic esters such as butyl acetate, methyl lactate and ethyl lactate; halogenated hydrocarbons such as 1,1,2-trichloroethylene; and high polar solvents such as dimethylacetamide, N-methylpyrrolidone, dimethylformamide and dimethyl sulfoxide. These solvents may be used singly or in combination with each other.

The positive-type photoresist composition of the present invention can comprise surface active agents to further improve coating properties such as striation.

Examples of such surface active agents include nonionic surface active agents such as polyoxyethylene alkyl ethers (e.g., polyoxyethylene lauryl ether, polyoxyethylene stearyl ether, polyoxyethylene cetyl ether, polyoxyethylene oleyl ether); polyoxyethylene alkylallyl ethers (e.g., polyoxyethylene octyl phenol ether and polyoxyethylene nonyl phenol ether); polyoxyethylene-polyoxypropylene block copolymers; sorbitan aliphatic esters (e.g., sorbitan monolaurate, sorbitan monopalmitate, sorbitan monostearate, sorbitan monooleate, sorbitan trioleate, sorbitan tristearate); and polyoxyethylene sorbitan aliphatic esters (e.g., polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate); fluorine-containing surface active agents such as F TOP EF301, EF303 and EF352 (available from Shinakita Kasei K. K.), Megafac F171 and F173 (available from Dainippon Ink and Chemicals Incorporated), Furorad FC430 and FC431 (available from Sumitomo 3M) and Asahi Guard AG710, Surflon S-382, SC101, SC102, SC-03, SC104, SC105 and SC106 (available from Asahi Glass Company Limited); Organosiloxane polymer KP341 (available from Shin-Etsu Chemical Industry Co., Ltd); and acrylic or methacrylic (co)-polymer Polyflow No. 75 and No. 95 (available from Kyoeisha Yushikagaku Kogyo Co., Ltd.). The content of such a surface active agent is normally in the range of about 2 parts by weight or less, preferably about 1 part by weight or less per 100 parts by weight of alkali-soluble resin and quinonediazido compound in the composition of the present invention.

These surface active agents can be used singly or in combination.

Examples of developers for the positive-type photoresist composition of the present invention include aqueous solutions of alkalis such as inorganic alkali (e.g., sodium hydroxide, potassium hydroxide, sodium carbonate, sodium silicate, sodium metasilicate, and aqueous ammonia); primary amines (e.g., ethylamine and n-propylamine); secondary amines (e.g., diethylamine and di-n-butylamine); tertiary amines (e.g., triethylamine and methyldiethylamine); alcoholamines (e.g., dimethylethanolamine and triethanolamine); quaternary ammonium salts (e.g., tetramethylammonium hydroxide and tetraethylammonium hydroxide); and cyclic amines (e.g., pyrrole and piperidine). These aqueous solutions of alkalis may further contain alcohol and surface active agents in proper amounts.

The positive-type photoresist composition of the present invention can comprise a dye, a plasticizer, and an adhesive aid as necessary. Specific examples of such additives include dyes such as methyl violet, crystal violet and malachite green; plasticizers such as stearic acid, acetal resin, phenoxy resin, and alkyd resins; and adhesive aids such as hexamethyl disilazane, and chloromethyl silane.

The above-mentioned positive-type photoresist composition can be coated by a proper coting means such as a spinner and coater on a substrate as commonly used in the production of precision integrated circuit elements (e.g., silicon/silicon dioxide-coated substrate), exposed to light through a predetermined mask, and then developed to obtain an excellent resist.

The present invention will be further described hereinafter by way of examples, but the present invention should not be construed as being limited thereto. The unit % indicates percent by weight unless otherwise defined. Also, unless otherwise indicated, all parts, ratios, and the like are by weight.

EXAMPLES 1 TO 4 AND COMPARATIVE EXAMPLES 1 TO 4

(1) Synthesis of novolak resin (A)

40 g of m-cresol, 60 g of p-cresol, 54.0 g of a 37% aqueous solution of formalin and 0.05 g of oxalic acid were charged into a three-necked flask. The material was then heated to a temperature of 100° C. with stirring, where it was allowed to undergo reaction for 7 hours. The reaction system was then cooled to room temperature of 200° C. so that its pressure was reduced to 30 mmHg. The reaction system was then gradually heated to a temperature of 150° C. to remove water and unreacted monomers therefrom. The novolak resin thus obtained exhibited an average molecular weight of 7,900 as calculated in terms of polystyrene.

(2) Synthesis of novolak resin (B)

A cresol novolak resin (molecular weight: 9,400 as calculated in terms of polystyrene) was synthesized from 50% by weight of m-cresol, 50% by weight of p-cresol and an aqueous solution of formalin in the same manner as conducted in the foregoing synthesis method (1). Low molecular weight components were then separated from the cresol novolak resin in accordance with Masayoshi Kinoshita and Takayuki Otsu, "Kobunshi Gosei no Jikkenho (Experimental Synthesis of High Molecular Compounds)", Kagaku Dojin, p. 32, 1973, to obtain a cresol novolak resin having a molecular weight of 10060 as calculated in terms of polystyrene.

(3) Synthesis of light-sensitive material a 11.5 g of 2,3,4-trihydroxybenzophenone, 30.2 g of 1,2-naphthoquinonediazide-5-sulfonyl chloride and 300 ml of acetone were charged into a three-necked flask to make a uniform solution. A mixture of 11.4 g of triethylamine and 50 ml of acetone was then gradually added dropwise to the reaction system. The reaction system was then allowed to undergo reaction at a temperature of 25° C. for 3 hours. The reaction mixture was then poured into 1,500 ml of a 1% aqueous solution of hydrochloric acid. The resulting precipitate was filtered off, washed with water, and then dried at a temperature of 40° C. to obtain 29.8 g of 1,2-naphthoquinonediazide-5l-sulfonic ester of 2,3,4-trihydroxybenzophenone.

(4) Synthesis of light-sensitive material b 12.3 g of 2,3,4,4'-tetrahydroxybenzophenone, 40.3 g of 1,2-naphthoquinonediazide-5-sulfonyl chloride and 300 ml of acetone were charged into a three necked flask to make a uniform solution. A mixture of 15.2 g of triethylamine and 50 ml of acetone was then gradually added dropwise to the reaction system. The reaction system was then allowed to undergo reaction at a temperature of 25° C. for 3 hours. The reaction mixture was then poured into 1,500 ml of a 1% aqueous solution of hydrochloric acid. The resulting precipitate was filtered off, washed with water, and then dried at a temperature of 40° C. to obtain 39.7 g of 1,2-naphthoquinonediazide-5-sulfonic ester of 2,3,4,4'-tetrahydroxybenzophenone.

(5) SYNTHESIS EXAMPLE 1: Synthesis of α,α,α',α',α'',α''-hexakis-(4-hydroxyphenyl)-1,3,5-triethylbenzene as Compound [I-a]

3.0 ml of thioglycolic acid was added to a melt mixture of 282 g of phenol and 30.6 g of 1,3,5-triacetylbenzene. Hydrogen chloride gas was then introduced into the reaction system at a temperature of 50° C. After infrared absorption spectrum and gas chromatography indicated the elimination of all of the starting material and hence the completion of the formation of hexaphenol, phenol was then distilled off from all the reaction products under reduced pressure. The reaction products were then recrystallized from aqueous methanol for purification. The resulting white crystal exhibited a purity of 97% by gas chromatography and a melting point of 172° to 178° C.

(6) SYNTHESIS EXAMPLE 2: Synthesis of α,α,α',α',α'',α''-hexakis-(4-hydroxy-3,5-dimethylphenyl)-1,3,5-triethylbenzene as Compound [I-b]

Compound [I-b] was synthesized in the same manner as Compound [I-a] in Synthesis Example 1, except that 366 g of 2,6-xylenol was used instead of phenol. The resulting white crystal exhibited a purity of 99% by gas chromatography and a melting point of 174° to 180° C.

scope for evaluation. The results are set forth in Table 3.

TABLE 1

| No. | Compounds used as additives |
|-----|-----------------------------|
|     | Compound |
| 1 | Compound [I-a] obtained in Synthesis Example (1) |
| 2 | Compound [I-b] obtained in Synthesis Example (2) |
| 3 | 2,3,4-Trihydroxybenzophenone |
| 4 | 2,3,4-Tetrahydroxybenzophenone |
| 5 | 2,3,4-Hexahydroxybenzophenone |

TABLE 2

| | Formulations of resist composition | | |
|---|---|---|---|
| Example No. | Novolak resin (g) | Light sensitive material (g) | Additive (g) |
| Example 1 | (A) 5 | (a) 1.25 | (1) 0.38 |
| Example 2 | (A) 5 | (a) 1.25 | (2) 0.34 |
| Example 3 | (A) 5 | (a) 1.35 | (1) 0.41 |
| Example 4 | (B) 5 | (a) 1.40 | (2) 0.39 |
| Comparative Example 1 | (A) 5 | (a) 1.25 | None — |
| Comparative Example 2 | (A) 5 | (a) 1.25 | (3) 0.38 |
| Comparative Example 3 | (A) 5 | (b) 1.25 | (4) 0.38 |
| Comparative Example 4 | (B) 5 | (b) 1.35 | (5) 0.41 |

TABLE 3

| | Results of Evaluation | | | | | |
|---|---|---|---|---|---|---|
| Example No. | Relative sensitivity | Film remaining (%) | Resolving power (μm) | Heat resistance (°C.) | Resist shape (Θ) | Developability |
| Example | | | | | | |
| 1 | 1.3 | 98 | 0.50 | 135 | 89 | E |
| 2 | 1.4 | 99 | 0.50 | 140 | 89 | E |
| 3 | 1.3 | 99 | 0.50 | 140 | 88 | E |
| 4 | 1.3 | 99 | 0.50 | 140 | 88 | E |
| Comparative Example | | | | | | |
| 1 | 1.0 | 98 | 0.52 | 135 | 85 | P |
| 2 | 1.1 | 95 | 0.52 | 125 | 82 | E |
| 3 | 1.1 | 97 | 0.52 | 130 | 83 | F |
| 4 | 1.0 | 95 | 0.55 | 135 | 82 | F |

(7) Preparation and evaluation of positive type photoresist composition

The cresol novolak resin (A) or (B) as prepared in the above mentioned procedure (1) or (2), the light-sensitive material a or b obtained in the above-mentioned procedure (3) or (4), and the additives (1) to (5) as set forth in Table 1 were dissolved in 15 g of ethyl cellosolve acetate in the proportion as set forth in Table 2. The material was filtered through a microfilter having a pore diameter of 0.2 μm to prepare a photoresist composition. The photoresist composition was coated on a silicon wafer by a spinner, and then dried by a vacuum hot plate at a temperature of 100° C. for 90 seconds to obtain a resist film having a thickness of 1.2 μm.

The resist film was exposed to light by means of a reduction projection exposing apparatus FPA-1550 available from Canon Inc., developed with a 2.38% aqueous solution of tetramethyl ammonium hydroxide for 1 minute, washed with water for 30 seconds, and then dried.

The resist pattern thus formed on the silicon wafer was observed under a scanning-type electron microscope for evaluation. The results are set forth in Table 3.

The sensitivity is defined as the reciprocal of the exposure reproducing a 0.70 μm mask pattern, represented relative to the value of Comparative Example 1.

The percent film remaining is represented by the percentage of film from before development retained after development.

The resolving power indicates the threshold resolving power at the exposure reproducing a 0.70 μm mask pattern.

The heat resistance indicates the temperature at which the silicon wafer on which a resist pattern has been formed shows no pattern deformation after baking in a convection oven for 30 minutes.

The resist shape is represented by the angle (θ) of the surface of the resist wall with the plane of the silicon wafer in the section of the 0.70 μm resist pattern.

For the evaluation of developability, E (excellent) indicates an excellent condition having no observed surface peeling and film residue, P (poor) indicates a poor condition having much observed surface peeling and film residue, and F (fair) indicates a fair condition having some observed surface peeling and film residue.

The results show that the resists comprising the additives (1) and (2) of the present invention were excellent in sensitivity, film remaining, resolving power, heat resistance, resist shape and developability.

EXAMPLES 5 TO 8 AND COMPARATIVE EXAMPLES 5 TO 8

(1) SYNTHESIS EXAMPLE 3: Synthesis of Compound [II-a]

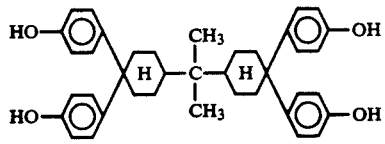

520 g of toluene, 602 g of phenol, and 189 g of 2,2-bis(4-oxocyclohexyl)propane were stirred at room temperature. 10 ml of n-octylmercaptane was added to the material. The reaction system was allowed to undergo reaction with dried hydrogen chloride gas bubbled thereinto. When 2 hours passed, the reaction system turned white. 520 g of toluene was added to the reaction system. The reaction system was then allowed to undergo reaction for 1 hour. Nitrogen gas was used to remove the hydrogen chloride gas from the system. The resulting crystal was filtered off, and then washed with hot water to obtain 437 g of light yellow powder. The powder was then recrystallized from ethyl ether for purification. The powder thus purified exhibited a purity of 99.8% and a melting point of 178° C. as a result of gas chromatography.

(2) SYNTHESIS EXAMPLE 4: Synthesis of Compound [II-b]

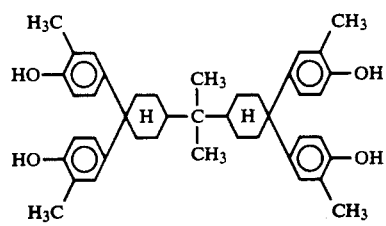

130 g of toluene, 173 g of o-cresol, and 47.2 g of 2,2-bis(4-oxocyclohexyl)propane were stirred at room temperature. 2.6 ml of octylmercaptane and 0.5 g of p-toluenesulfonic acid were then added to the material. The reaction system was then allowed to undergo reaction at a temperature of 50° C. for 2 hours. 0.5 g of p-toluenesulfonic acid was then added to the reaction system. The reaction system was further allowed to undergo reaction for 2 hours. The reaction product was washed with saturated brine, dehydrated, and then dried. Cresol and toluene were then removed from the system by means of an evaporator. The product was then recrystallized from cyclohexanone to obtain 115 g of a white powder having a purity of 99.3% and a melting point of 169° C.

(3) SYNTHESIS EXAMPLE 5: Synthesis of Compound [II-k]

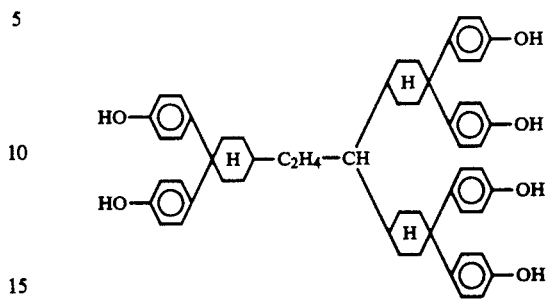

489 g of toluene, 565 g of phenol, 165 g of 1,1,3-tris(4-oxocyclohexyl)propane, and 6.5 ml of octylmercaptane were stirred at room temperature. The reaction system was allowed to undergo reaction with dried hydrogen chloride gas bubbled thereinto for 1 hour. The reaction system was further allowed to undergo reaction at a temperature of 70° C. for 2 hours. 489 g of toluene was then added to the reaction system. The reaction system was further allowed to undergo reaction for 2 hours. Hydrogen chloride gas was then removed from the system. The resulting crystal was filtered off, washed with toluene and hot water, and then dehydrated and dried. The material was then recrystallized from a mixture of toluene and methanol to obtain 401 g of a light yellow powder having a purity of 96.7% and a melting point of 204° C.

(4) Preparation and evaluation of positive type photoresist composition

The cresol novolak resin (A) or (B) as prepared in procedure (1) or (2) of Example 1, the light-sensitive material a or b obtained in procedure (3) or (4) of Example 1, and the additives (6) to (11) as set forth in Table 4 were dissolved in 15 g of ethyl cellosolve acetate in the proportion as set forth in Table 5. The material was filtered through a microfilter having a pore diameter of 0.2 μm to prepare a photoresist composition. The photoresist composition was coated on a silicon wafer by a spinner, and then dried by a vacuum hot plate at a temperature of 100° C. for 90 seconds to obtain a resist film having a thickness of 1.2 μm.

The resist film was exposed to light by means of reduction projection exposing apparatus FPA-1550 available from Canon Inc., developed with a 2.38% aqueous solution of tetramethyl ammonium hydroxide for 1 minute, washed with water for 30 seconds, and then dried.

The resist pattern thus formed on the silicon wafer was observed under a scanning type electron microscope for evaluation. The results are set forth in Table 6.

TABLE 4

| | Compounds used as additives |
|---|---|
| No. | Compound |
| 6 | Compound [II-a] obtained in Synthesis Example (3) |
| 7 | Compound [II-b] obtained in Synthesis Example (4) |
| 8 | Compound [II-k] obtained in Synthesis Example (5) |
| 9 | 2,3,4-Trihydroxybenzophenone |
| 10 | 2,3,4-Tetrahydroxybenzophenone |
| 11 | 2,3,4-Hexahydroxybenzophenone |

TABLE 5

| Example No. | Formulations of resist composition | | |
|---|---|---|---|
| | Novolak resin (g) | Light sensitive material (g) | Additive (g) |
| Example 5 | (A) 5 | (a) 1.25 | (6) 0.38 |
| Example 6 | (A) 5 | (a) 1.25 | (7) 0.34 |
| Example 7 | (A) 5 | (a) 1.35 | (8) 0.41 |
| Example 8 | (B) 5 | (a) 1.40 | (7) 0.39 |
| Comparative Example 5 | (A) 5 | (a) 1.25 | None — |
| Comparative Example 6 | (A) 5 | (a) 1.25 | (9) 0.38 |
| Comparative Example 7 | (A) 5 | (b) 1.25 | (10) 0.38 |
| Comparative Example 8 | (B) 5 | (b) 1.35 | (11) 0.41 |

TABLE 6

| Example No. | Results of Evaluation | | | | | |
|---|---|---|---|---|---|---|
| | Relative sensitivity | Film remaining (%) | Resolving power (μm) | Heat resistance (°C.) | Resist shape (Θ) | Developability |
| Example | | | | | | |
| 5 | 1.3 | 98 | 0.50 | 140 | 89 | E |
| 6 | 1.4 | 99 | 0.50 | 140 | 89 | E |
| 7 | 1.4 | 99 | 0.50 | 140 | 88 | E |
| 8 | 1.3 | 99 | 0.50 | 145 | 89 | E |
| Comparative Example | | | | | | |
| 5 | 1.0 | 98 | 0.52 | 135 | 85 | P |
| 6 | 1.1 | 95 | 0.52 | 125 | 82 | E |
| 7 | 1.1 | 97 | 0.52 | 130 | 83 | F |
| 8 | 1.0 | 95 | 0.55 | 135 | 82 | F |

The sensitivity is defined as the reciprocal of the exposure reproducing a 0.70 μm mask pattern, represented relative to the value of Comparative Example 5.

The percent film remaining, the resolving power, the heat resistance, the resist shape and the developability were evaluated in the same manner as in Example 1.

The results show that the resists comprising the additives (6) to (8) of the present invention were excellent in sensitivity, film remaining, resolving power, heat resistance, resist shape and developability.

EXAMPLES 9 TO 12 AND COMPARATIVE EXAMPLES 9 TO 12

(1) SYNTHESIS EXAMPLE 6: Synthesis of Compound [III-b]

188 g (2.0 mol) of phenol was added to 25.4 g (0.20 mol) of dichloroacetone. The admixture was heated to a temperature of 45° C. Hydrogen chloride gas was introduced into the reaction solution. When the reaction solution turned yellow, heating was suspended, and the introduction of hydrogen chloride gas continued for 2 hours. The resulting reddish brown reaction mixture was distilled under reduced pressure to remove excess phenol. The resulting reddish brown solid residue was washed with n-hexane, and then purified through column chromatography (filler: silica gel; eluant: n-hexane/ethyl acetate=2/1). As a result, 72 g of a white powder was obtained. The powder was confirmed by NMR (nuclear magnetic resonance) to be 1,2,2,3-tetrakis(4'-hydroxyphenyl)propane [III-b].

(2) SYNTHESIS EXAMPLE 7: Synthesis of Compound [III-c]

A mixture of 66.5 g (0.40 mol) of 4-hydroxyphenylpropionic acid and 16.4 g (0.12 mol) of zinc chloride was heated to a temperature of 140° C. to make solution. 75.3 g (0.80 mol) of phenol was added to the solution. The admixture was stirred at a temperature of 140° C. for 6 hours. The resulting reddish brown reaction mixture was put into 1.5 l of ice-water. The material was then extracted with ethyl acetate. The extract was dried, and then concentrated. The resulting dark brown viscous oil was then purified through column chromatography (filler: silica gel; eluant: n-hexane/ethyl acetate=4/1). As a result, 55 g of a white powder (1,3-bis(4'-hydroxyphenyl)-1-propane) having the following chemical structure:

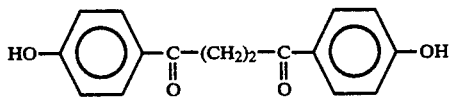

was obtained.

188 g (2.0 mol) of phenol and 1 ml of thioglycolic acid were added to 48.5 g of 1,3-bis(4'-hydroxyphenyl)-1-propanone. The admixture was heated to a temperature of 50° C. Hydrogen chloride gas was introduced into the reaction system for 7 hours. The reaction system was stirred at a temperature of 50° C. for 10 hours. The resulting dark brown reaction mixture was distilled under reduced pressure to remove excess phenol. The resulting dark brown solid was purified through column chromatography (filler: silica gel; eluant: n-hexane/ethyl acetate=3/1). As a result, 43 g of a white powder was obtained. The white powder was then confirmed by NMR to be 1,1,1,3-tetrakis(4'-hydroxyphenyl)propane [III-c].

(3) SYNTHESIS EXAMPLE 8: Synthesis of Compound [III-m]

A mixture of 52.8 g (0.40 mol) of glutaric acid and 32.7 g (0.24 mol) of lead chloride was heated to a temperature of 140° C. to make a solution. 151 g (1.6 mol) of phenol was added to the solution. The admixture was stirred at a temperature of 140° C. for 6 hours. The resulting reddish brown reaction mixture was put into 1.5 l of ice-water. The material was then extracted with ethyl acetate. The extract was dried, and then concentrated. The resulting dark brown viscous oil was then purified through column chromatography (filler: silica gel; eluant: n-hexane/ethyl acetate=3/1). As a result, 59 g of a white powder (1,5-bis(4'-hydroxyphenyl)-1,5-pentadione) having the following chemical structure:

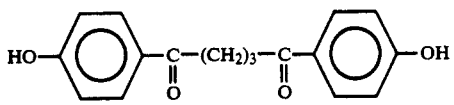

was obtained.

376 g (4.0 mol) of phenol and 2 ml of thioglycolic acid were added to 56.9 g of 1,5-bis(4'-hydroxyphenyl)-1,5-pentanedione. The admixture was heated to a temperature of 50° C. Hydrogen chloride gas was introduced into the reaction system for 8 hours. The reaction system wa stirred at a temperature of 50° C. for 12 hours. The resulting dark brown reaction mixture was distilled under reduced pressure to remove excess phenol. The resulting dark brown solid was purified through column chromatography (filler: silica gel; eluant: n-hexane/ethyl acetate=2/1). As a result, 56 g of a white powder was obtained. The white powder was then confirmed by NMR to be 1,1,1,5,5,5-hexakis(4'-hydroxyphenyl)pentane [III-m].

(4) Preparation and evaluation of positive type photoresist composition

The cresol novolak resin (A) or (B) as prepared in procedure (1) or (2) of Example 1, the light-sensitive material a or b obtained in procedure (3) or (4) of Example 1, and the additives (12) to (17) as set forth in Table 7 were dissolved in 15 g of ethyl cellosolve acetate in the proportion as set forth in Table 8. The material was filtered through a microfilter having a pore diameter of 0.2 μm to prepare a photoresist composition. The photoresist composition was coated on a silicon wafer by a spinner, and then dried by a vacuum hot plate at a temperature of 100° C. for 90 seconds to obtain a resist film having a thickness of 1.2 μm.

The resist film was exposed to light by means of a reduction projection exposing apparatus FPA-1550 available from Canon Inc., developed with a 2.38% aqueous solution of tetramethyl ammonium hydroxide for 1 minute, washed with water for 30 seconds, and then dried.

The resist pattern thus formed on the silicon wafer was observed under a scanning type electron microscope for evaluation. The results are set forth in Table 9.

TABLE 7

| No. | Compound |
|---|---|
| 12 | Compound [III-b] obtained in Synthesis Example (6) |
| 13 | Compound [III-c] obtained in Synthesis Example (7) |
| 14 | Compound [III-m] obtained in Synthesis Example (8) |
| 15 | 2,3,4-Trihydroxybenzophenone |
| 16 | 2,3,4-Tetrahydroxybenzophenone |
| 17 | 2,3,4-Hexahydroxybenzophenone |

TABLE 8

| Example No. | Novolak resin (g) | Light-sensitive material (g) | Additive (g) |
|---|---|---|---|
| Example 9 | (A) 5 | (a) 1.25 | (12) 0.38 |
| Example 10 | (A) 5 | (a) 1.25 | (13) 0.34 |
| Example 11 | (A) 5 | (a) 1.35 | (14) 0.38 |
| Example 12 | (B) 5 | (a) 1.40 | (13) 0.39 |
| Comparative Example 9 | (A) 5 | (a) 1.25 | None — |
| Comparative Example 10 | (A) 5 | (a) 1.25 | (15) 0.38 |
| Comparative Example 11 | (A) 5 | (b) 1.25 | (16) 0.38 |
| Comparative Example 12 | (B) 5 | (b) 1.35 | (17) 0.41 |

TABLE 9

| Example No. | Relative sensitivity | Film remaining (%) | Resolving power (μm) | Heat resistance (°C.) | Resist shape (Θ) | Developability |
|---|---|---|---|---|---|---|
| Example | | | | | | |
| 9 | 1.4 | 98 | 0.50 | 140 | 89 | E |
| 10 | 1.3 | 99 | 0.50 | 140 | 89 | E |
| 11 | 1.3 | 99 | 0.50 | 140 | 89 | E |
| 12 | 1.3 | 99 | 0.50 | 150 | 88 | E |
| Comparative Example | | | | | | |
| 9 | 1.0 | 98 | 0.52 | 135 | 85 | P |
| 10 | 1.1 | 95 | 0.52 | 125 | 82 | E |
| 11 | 1.1 | 97 | 0.52 | 130 | 83 | F |
| 12 | 1.0 | 95 | 0.55 | 135 | 82 | F |

The sensitivity is defined as the reciprocal of the exposure reproducing a 0.70 μm mask pattern, represented relative to the value of Comparative Example 9.

The percent film remaining, the resolving power, the heat resistance, the resist shape and the developability were evaluated in the same manner as in Example 1.

The results show that the resists comprising the additives (12) to (14) of the present invention are excellent in sensitivity, percent film remaining, resolving power, heat resistance, resist shape, and developability.

As can be seen from the above, the positive photoresist according to the present invention is excellent in resolving power, sensitivity, developability and heat resistance and thus is suitable for use in fine work.

While the invention has been described in detail and with reference to specific embodiments thereof, it will be apparent to one skilled in the art that various changes and modifications can be made therein without departing from the spirit and scope thereof.

What is claimed is:

1. A positive photoresist composition, which comprises in admixture an alkali-soluble resin, a quinonediazide compound and a compound selected from the group consisting of compounds represented by formulae (I), (II) and (III):

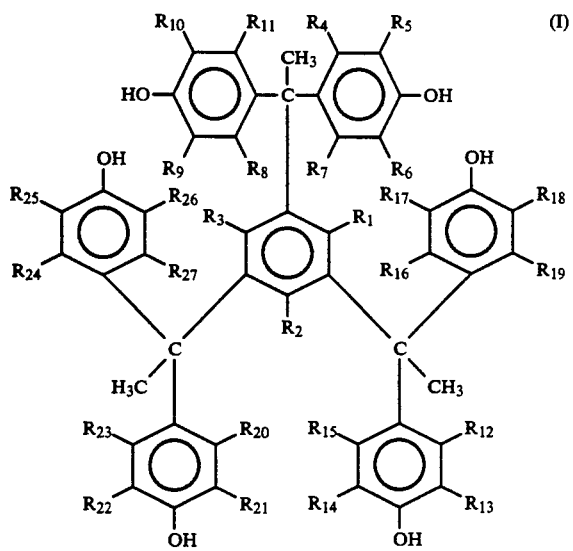
(I)

wherein $R_1$ to $R_{27}$, which may be the same or different, each represents a hydrogen atom, hydroxyl group, halogen atom, alkyl group, alkoxy group, nitro group, alkenyl group, aryl group, aralkyl group, alkoxycarbonyl group, arylcarbonyl group, acyloxy group, acyl group, aryloxy group or aralkoxy group;

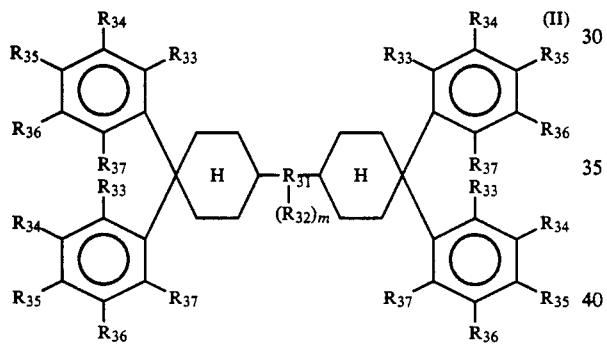
(II)

wherein $R_{31}$ represents an organic group, single bond,

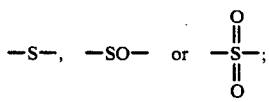

$R_{32}$ represents a hydrogen atom, monovalent organic group or

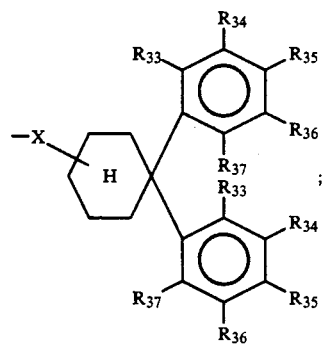

$R_{33}$ to $R_{37}$, which may be the same or different and in which four groups represented by $R_{33}$ are the same or different, four groups represented by $R_{34}$ are the same or different, four groups represented by $R_{35}$ are the same or different, four groups represented by $R_{36}$ are the same or different, four groups represented by $R_{37}$ are the same or different, each represents a hydrogen atom, hydroxyl group, halogen atom, alkyl group, alkoxy group or alkenyl group, with the proviso that at least one of $R_{33}$ to $R_{35}$ is a hydroxyl group; X represents a divalent organic group; and m represents an integer 0 or 1, with the proviso that m is 1 only when $R_{31}$ represents an organic group;

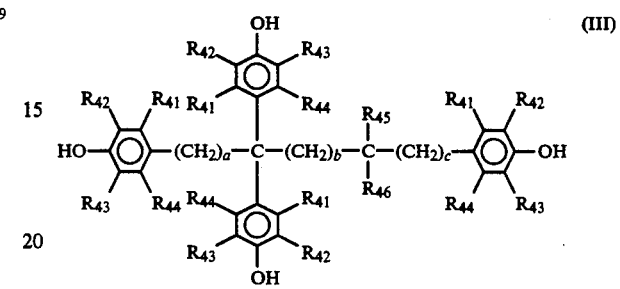
(III)

wherein $R_{41}$ to $R_{44}$, which may be the same or different and in which four groups represented by $R_{41}$ are the same or different, four groups represented by $R_{42}$ are the same or different, four groups represented by $R_{43}$ are the same or different, and four groups represented by $R_{44}$ are the same or different, each represents a hydrogen atom, hydroxyl group, halogen atom, alkyl group, alkoxy group or alkenyl group; $R_{45}$ and $R_{46}$ each represents a hydrogen atom, alkyl group or

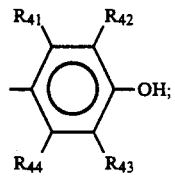

a and c each represents an integer 0 or 1; and b represents an integer from 1 to 4;

wherein the compound selected from the group consisting of compounds represented by formulae (I), (II) and (III) is present in an amount of about 150 parts by weight or less per 100 parts by weight of the quinonediazide compound; and wherein the quinonediazide compound is present in an amount of about 5 to about 100 parts by weight per 100 parts by weight of the alkali-soluble resin.

2. A positive photoresist composition as in claim 1, wherein the compound selected from the group consisting of compounds represented by formulae (I), (II) and (III) is present in an amount of from 5 to 100 parts by weight per 100 parts by weight of the quinonediazide compound.

3. A positive photoresist composition as in claim 1, wherein the alkali-soluble resin is a novolak resin.

4. A positive photoresist composition as in claim 1, wherein the alkali-soluble resin is a novolak resin having a weight average molecular weight in the range of from about 2,000 to about 30,000.

5. A positive photoresist composition as in claim 1, wherein the alkali-soluble resin is a novolak resin having a weight average molecular weight in the range of from about 6,000 to about 20,000.

* * * * *